United States Patent
Avellanet et al.

(10) Patent No.: US 7,195,636 B2
(45) Date of Patent: Mar. 27, 2007

(54) ANEURYSM NECK COVER FOR SEALING AN ANEURYSM

(75) Inventors: Ernesto Avellanet, Miami Lakes, FL (US); Robert Lulo, Pembroke Pines, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 556 days.

(21) Appl. No.: 10/295,164

(22) Filed: Nov. 15, 2002

(65) Prior Publication Data

US 2003/0093108 A1 May 15, 2003

Related U.S. Application Data

(60) Provisional application No. 60/335,608, filed on Nov. 15, 2001.

(51) Int. Cl.
*A61B 17/08* (2006.01)

(52) U.S. Cl. ..................................... 606/151

(58) Field of Classification Search ............... 606/151, 606/157, 215, 216, 158
See application file for complete search history.

(56) References Cited

U.S. PATENT DOCUMENTS

| | | | |
|---|---|---|---|
| 4,641,379 A | 2/1987 | Martin | |
| 4,653,124 A | 3/1987 | McNeal et al. | |
| 5,048,516 A | 9/1991 | Soderberg | |
| 5,108,420 A | 4/1992 | Marks | |
| 5,192,301 A | 3/1993 | Kamiya et al. | |
| 5,704,063 A | 1/1998 | Tilden | |
| 5,733,294 A | 3/1998 | Forber et al. | |
| 5,741,297 A * | 4/1998 | Simon | 606/151 |
| 5,895,410 A * | 4/1999 | Forber et al. | 606/200 |
| 5,904,703 A | 5/1999 | Gilson | |
| 6,036,720 A | 3/2000 | Abrams et al. | |
| 6,063,100 A | 5/2000 | Diaz et al. | |
| 6,063,111 A | 5/2000 | Hieshima et al. | |
| 6,085,748 A | 7/2000 | Sword et al. | |
| 6,113,622 A | 9/2000 | Hieshima | |
| 6,171,329 B1 | 1/2001 | Shaw et al. | |
| 6,183,491 B1 | 2/2001 | Lulo | |
| 6,214,029 B1 | 4/2001 | Thill et al. | |

(Continued)

FOREIGN PATENT DOCUMENTS

EP 0545091 A2 6/1993

(Continued)

OTHER PUBLICATIONS

European Search Report EP 02257918.9 dated Jan. 31, 2003.

(Continued)

*Primary Examiner*—Kevin T. Truong
(74) *Attorney, Agent, or Firm*—Henry W. Collins (57) ABSTRACT

An aneurysm neck cover is disclosed for use in occluding the flow of blood within an aneurysm. The aneurysm neck cover includes a first and second expandable sealing member having a circular joining member and reinforcing spokes which give the sealing members a slightly cupped configuration. The expandable sealing members are connected with a support element. When the aneurysm neck cover is deployed within the aneurysm, the first sealing member expands within the aneurysm while the second sealing member expands within an adjacent blood vessel thereby forming a seal around the mouth of the aneurysm and preventing the flow of blood within the aneurysm.

22 Claims, 4 Drawing Sheets

U.S. PATENT DOCUMENTS

| | | |
|---|---|---|
| 6,254,612 B1 | 7/2001 | Hieshima |
| 6,340,023 B2 | 1/2002 | Elkins |
| 6,397,847 B1 | 6/2002 | Scarberry et al. |
| 6,428,558 B1 | 8/2002 | Jones et al. |
| 6,651,663 B2 | 11/2003 | Barnett et al. |
| 6,748,949 B2 | 6/2004 | Smaldone |
| 6,811,560 B2 | 11/2004 | Jones et al. |
| 2005/0033408 A1 | 2/2005 | Jones et al. |

FOREIGN PATENT DOCUMENTS

| | | |
|---|---|---|
| WO | WO 01/10306 A1 | 8/1999 |

OTHER PUBLICATIONS

International Search Report for PCT/US04/36435, dated Dec. 19, 2005.

* cited by examiner

ANEURYSM NECK COVER FOR SEALING AN ANEURYSM

This patent application claims the benefit of provisional patent application Ser. No. 60/335,608 filed on Nov. 15, 2001.

BACKGROUND OF THE INVENTION

1. Field of the Invention

This invention relates to catheter-based implantable medical devices for occluding the flow of blood at a preselected position within a blood vessel, and more particularly to an aneurysm neck cover which serves to seal the mouth of an aneurysm thereby preventing the flow of blood into the aneurysm.

2. Description of the Prior Art

Aneurysms typically take the form of a balloon-like swelling in the wall of a vessel which generally results from a weakness in the vessel wall. If untreated, aneurysms may continue expanding until they burst thereby causing hemorrhaging to occur. If, for example, an aneurysm is present within an artery of the brain, and the aneurysm should burst with resulting cranial hemorrhaging, death could occur.

Aneurysms result from many different causes; however, most aneurysms are caused as a result of a degenerative disease which damages the muscular coating of a vessel with resulting congenital deficiency in the muscular wall of the vessel.

Various attempts have been made to treat aneurysms without resorting to surgery, such as the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Balloon expandable stents and self-expanding stents are generally delivered to a preselected position through a delivery catheter. They are moved out of the distal end of the delivery catheter, are expanded and then are released to remain within the vessel. One example of a delivery catheter system which may be used to place a stent within a vessel is disclosed in U.S. Pat. No. 6,254,612 entitled, "Hydraulic Stent Deployment System" and assigned to the same assignee as the present patent application. The stent deployment system disclosed in this patent, which is incorporated herein by reference, includes a deployment catheter having a distal tip for retaining a stent in order to transport the stent to a preselected position within the vessel. Once the stent has been properly positioned, a hydraulic control mechanism is used to release the stent from the distal end of the catheter and deposit the stent at the preselected location within the vessel.

Another method for treating aneurysms, particularly where the aneurysm occurs in a very small vessel of the brain, is that of using a microcatheter for placing multiple very small embolic coils within the aneurysm with the expectation that fibrous material will become entrapped in the embolic coils to thereby stabilize the coils within the aneurysm. With this technique, it is possible to fill the aneurysm with embolic coils thereby sealing off the walls of the aneurysm from the pressure of blood which exist in the adjacent vessel.

Examples of a catheter deployment system for depositing embolic coils into an aneurysm are disclosed in U.S. Pat. No. 6,063,100, entitled, "Embolic Coil Deployment System With Improved Embolic Coil"; U.S. Pat. No. 6,183,491 entitled, "Embolic Coil Deployment System With Improved Embolic Coil"; and U.S. Pat. No. 6,113,622 entitled, "Embolic Coil Hydraulic Deployment System," all of which are assigned to the assignee of the present patent application. These patents, and the disclosure thereof, are incorporated herein by reference and made a part of the present patent application.

One modification to the technique of placing embolic coils within an aneurysm is that of using a stent or scaffold like structure which is placed across the aneurysm by having passageways within the structures so that embolic coils may be passed through the structure and into the aneurysm. The stent, or scaffold like structure, serves to hold the embolic coils within the stent until such time as these coils become stabilized by fibrous material growing into the coils. One example of such a structure, or stent, for use in this form of treatment of an aneurysm is disclosed in U.S. Pat. No. 6,063,111 entitled, "Stent Aneurysm Treatment System And Method."

Still another method of treating an aneurysm, and in particular an aneurysm within the brain, is that of placing a mesh covered support structure within the aneurysm itself and subsequently expanding the mesh covered structure in order to fill the entire aneurysm. Such a structure serves to fill the aneurysm and thereby prevent blood flowing in an adjacent vessel from entering the aneurysm. These devices, referred to as occlusion devices, serve to prevent the pressure of blood flowing through a vessel from being applied to the walls of the aneurysm thereby preventing, or reducing, the further expansion of the aneurysm.

One such aneurysm occlusion or embolization device is disclosed in U.S. patent application Ser. No. 09/505,231 entitled, "Aneurysm Embolization Device," and assigned to the same assignee as the present patent application.

Even with the existing treatment techniques for aneurysms, and in particular for aneurysm which exists within the brain, there is a need for other forms of aneurysm treatment that may be easily delivered to a vascular site through a very small catheter, and in particular for a device which serves to seal off the flow of blood between an adjacent vessel and an aneurysm.

SUMMARY OF THE INVENTION

In accordance with one aspect of the present invention, there is provided a catheter-based aneurysm neck cover system for occluding the flow of blood into an aneurysm. The aneurysm neck cover system includes a deployment catheter. The neck cover system also includes a sheath which is disposed about the deployment catheter. The neck cover system further includes an aneurysm neck cover having first and second expandable sealing members. The sealing members each include a circular joining member and a plurality of reinforcing spokes attached to the circular joining member and extending radially outward from the joining member. A thin circular membrane is bonded to the circular joining member and to the reinforcing spokes to form a generally umbrella-like structure. A support element is attached to the center of the first sealing member to the center of the second sealing member. A headpiece is attached to the center of the second sealing members and is retained by the distal end of the deployment catheter so that the deployment catheter may be used to place the aneurysm neck cover at a mouth of an aneurysm and the sealing members may be expanded to seal the mouth of the aneurysm to prevent the flow of blood into the aneurysm.

In accordance with another aspect of the present invention, the expandable sealing members include first and second circular membranes having surfaces which are bonded together and which encapsulate the circular joining member and the reinforcing spokes.

In accordance with still another aspect of the present invention, the expandable sealing members are slightly cupped to form a convex side and a concave side. The convex side of the first expandable sealing member is attached to the distal end of the support element and the convex side of the second expandable sealing member is attached to the proximal end of the support element. Alternatively, the concave side of the first expandable sealing element may be attached to the distal end of the support element and the concave side of the second expandable sealing element is attached to the proximal end of the support element.

In accordance with a further aspect of the present invention, the circular joining member and the reinforcing spokes are made from a metallic material. The circular membrane is made from a blood-impermeable polymer material.

In accordance with another aspect of the present invention, the expandable sealing members are collapsed into a generally tubular shape when the sealing members are disposed within the lumen of the sheath.

DESCRIPTION OF THE PREFERRED EMBODIMENT

Figure 1:
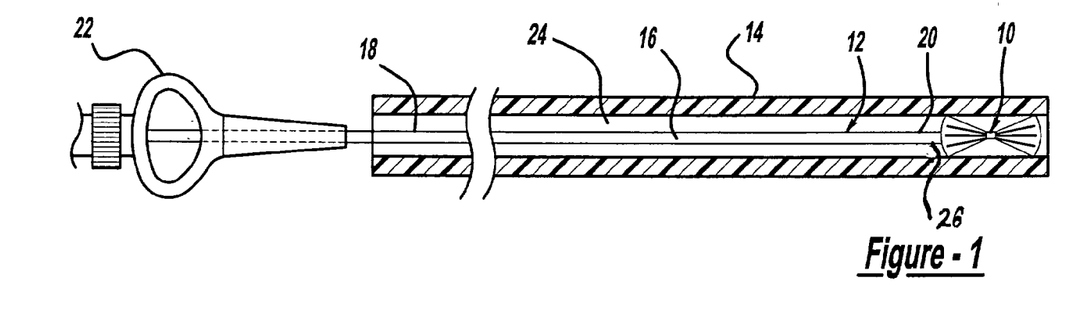
FIG. 1 is an enlarged perspective view of an aneurysm neck cover, a deployment catheter, and a sheath in accordance with the present invention.

FIG. 1 illustrates an aneurysm neck cover 10, a deployment catheter 12, and a sheath 14. The deployment catheter 12 is an elongated tube with a lumen 16. Preferably, the proximal section 18 of the deployment catheter 12 is formed of a pellethane material having a durometer in a range of about 60 D to 75 D. The proximal section 18 is sufficiently flexible to transverse the vasculature of the human body, but is sufficiently rigid so that it can be pushed distally through the sheath 14. The distal section 20 of the deployment catheter 12 is preferably formed of a pellethane material having a durometer of between 25 D and 55 D with a durometer of 40 D being the preferred durometer.

The deployment catheter 12 also includes a winged hub 22 coupled to the proximal section 18 of the deployment catheter 12. The winged hub 22 may be made from plastic and aids in the insertion of the deployment catheter 12 into the vasculature of the body. The sheath 14 is also an elongated tube with a lumen 24 extending therethrough. The sheath 14 is preferably formed of a polymer material and is sufficiently flexible to transverse the vasculature of the body. The deployment catheter 12 and aneurysm neck cover 10 are disposed within the lumen 24 of the sheath 14. The diameter of the lumen 24 on the sheath 14 is sufficiently small enough so that the aneurysm neck cover 10 is compressed to a collapsed configuration. The aneurysm neck cover 10 is attached to the distal end 26 of the deployment catheter 12 by way of a headpiece 28 which is described in more detail below.

Figure 2:
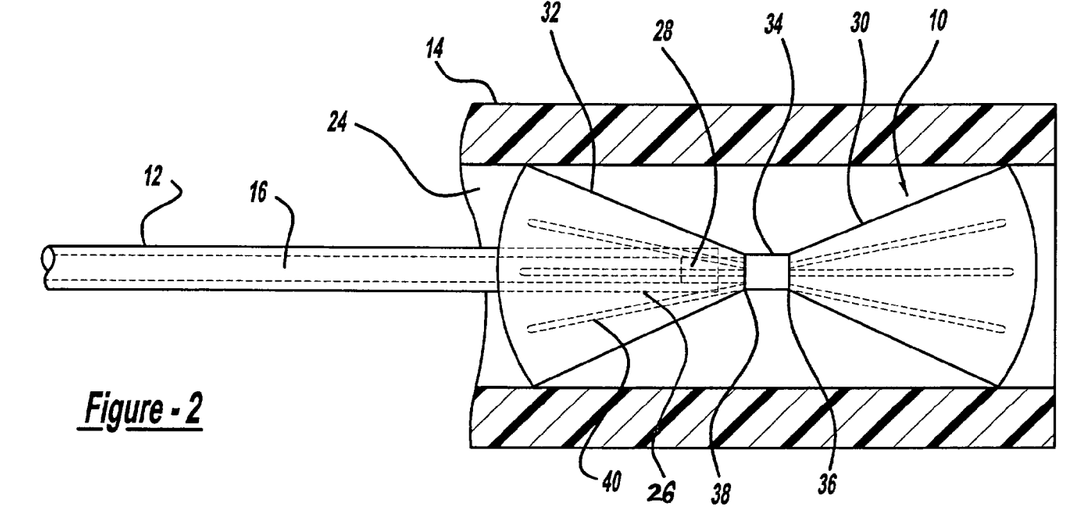
FIG. 2 is an enlarged, sectional view of the aneurysm neck cover in a collapsed configuration within a lumen of the sheath and attached to a distal end of the deployment catheter.

FIG. 2 illustrates the aneurysm neck cover 10 in a collapsed configuration within the lumen 24 of the sheath 14. The aneurysm neck cover 10 includes a first expandable sealing member 30 and a second expandable sealing member 32 connected by a support element 34. The first sealing member 30 is attached to the distal end 36 of the support element 34, while the second sealing member 32 is attached to the proximal end 38 of the support element 34. The expandable sealing members 30 and 32, in a collapsed configuration, are generally tubular-shaped such that the aneurysm neck cover 10 may be disposed within a sheath 14. There is a plurality of longitudinal reinforcing spokes 40 within each expandable sealing member 30 and 32. These reinforcing spokes 40 are discussed in the description of FIG. 3a. The headpiece 28 is attached to the second sealing member 32 and is disposed within the distal end 26 of the deployment catheter 12. The headpiece 28 forms a fluid tight seal in the distal end 26 of the deployment catheter 12 so that when a fluid pressure is applied to the lumen 16 of the deployment catheter 12, the headpiece 28 is released from the distal end 26 of the deployment catheter 12.

Figure 3:
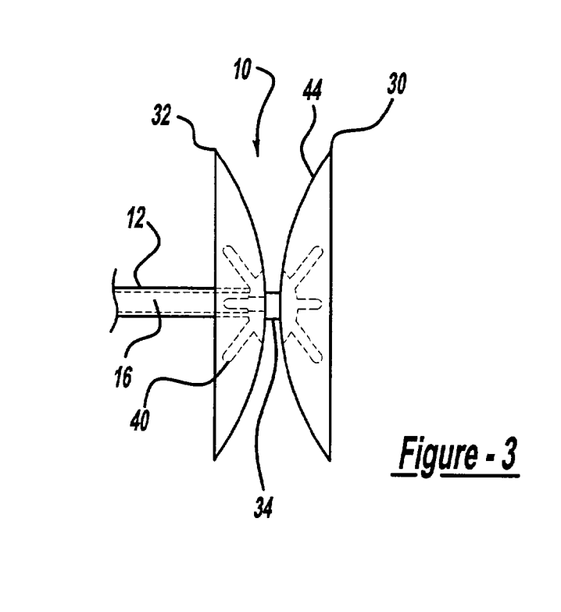
FIG. 3 is an enlarged, perspective view of the aneurysm neck cover in an expanded configuration.
Figure 6:
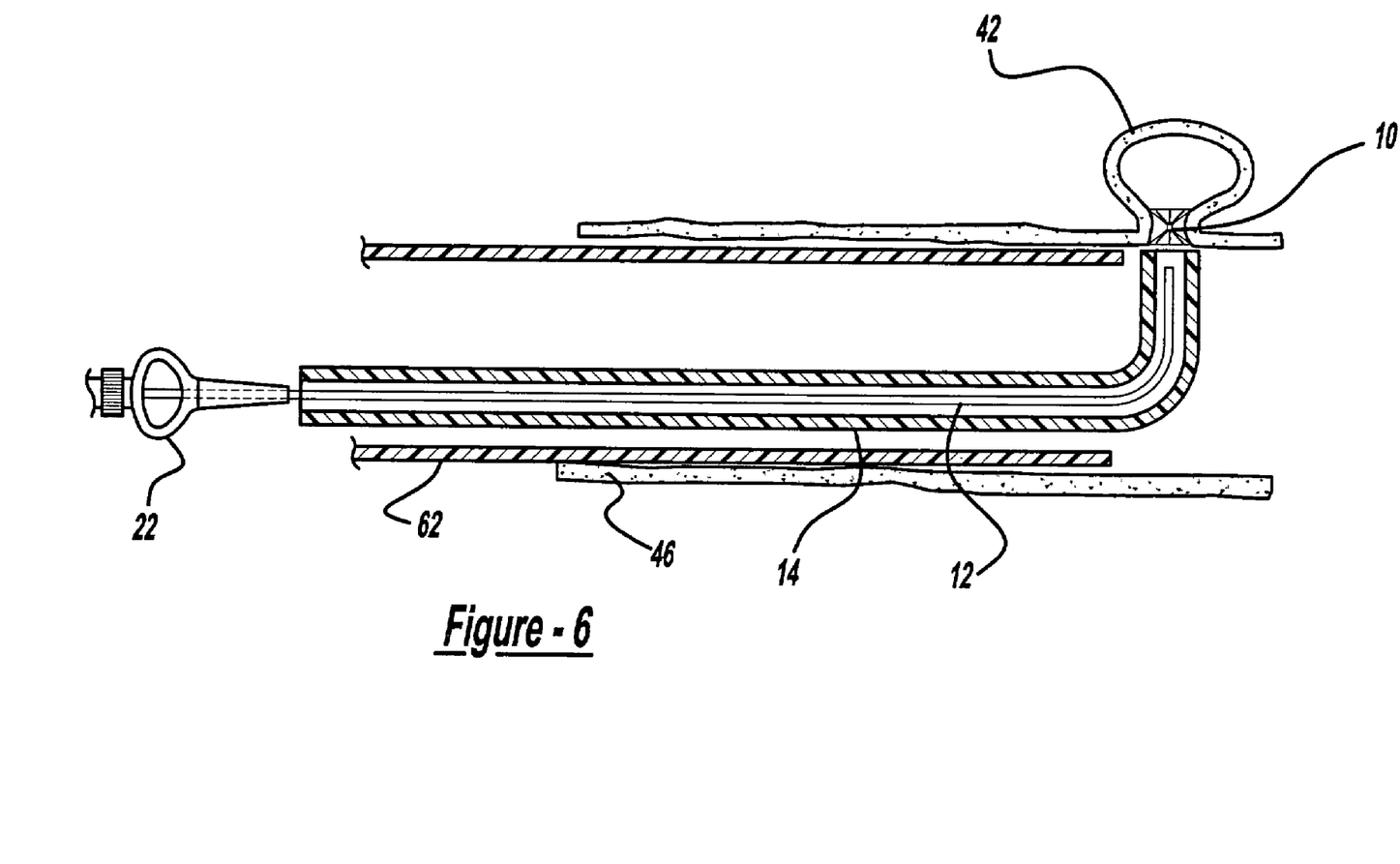

FIG. 3 illustrates the aneurysm neck cover 10 in an expanded configuration. The expandable sealing members 30 and 32 are preferably made of a flexible material like a polymer, silicon, or fabric, but may also be formed from metallic material such as platinum or Nitinol. The expandable sealing members 30 and 32 may also include radiopaque material for fluoroscopic visualization. Preferably, the sealing members 30 and 32 are slightly cupped so that, as illustrated in FIG. 6, when the first sealing member 30 is deployed within an aneurysm 42, the convex side 44 of the first sealing member 30 conforms to a wall of the aneurysm 42 and when the second sealing member 32 is deployed within an adjacent blood vessel 46 of the aneurysm 42, the convex side 44 of the second sealing member 32 conforms to a wall of the blood vessel 46.

The sealing members 30 and 32 may also be cupped in a reverse direction such that when the first sealing member 30 is deployed within the aneurysm 42, the outer edge 48 of the first sealing member 30 conforms to the wall of the aneurysm 42, and when the second sealing member 32 is deployed within the adjacent blood vessel 46, the outer edge 48 of the second sealing member 32 conforms to the wall of the blood vessel 46. The diameter of the sealing members 30 and 32 is generally slightly larger than the diameter of the opening of the aneurysm 42. Preferably, the sealing members 30 and 32 will seal the opening of a 5 to 6 mm aneurysm, but may vary in size to seal aneurysms in the range of 3 to 20 mm. The support element 34 connects the expandable sealing members 30 and 32 together. The support element 34 may be made of the same material as the expandable sealing members 30 and 32.

Figure 3A:
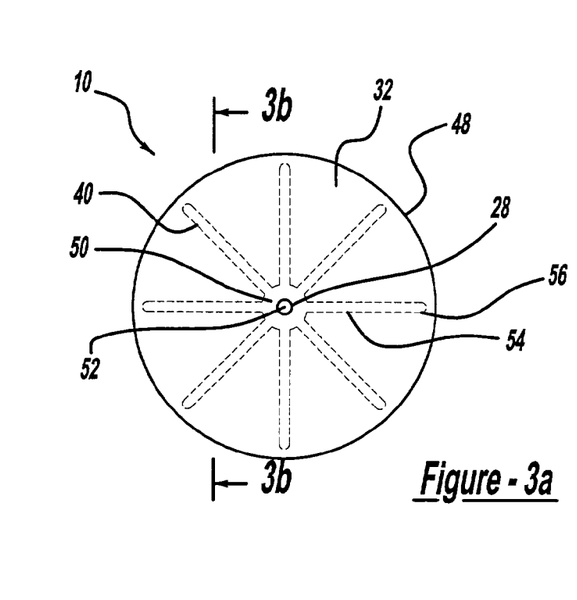
FIG. 3a is an enlarged, perspective view of the aneurysm neck cover as viewed from a distal end of the deployment catheter.

FIG. 3a illustrates the aneurysm neck cover 10 in an expanded configuration as viewed from within the blood vessel 46 adjacent to the aneurysm 42. A thin circular joining member 50 is disposed at the center 52 of each sealing member 30 and 32 and connects each sealing member 30 and 32 to the support element 34. The circular joining member 50 may be made of stainless steel, titanium, platinum, or a polymer material, but the preferred material is Nitinol. The plurality of reinforcing spokes 40 extends radially outward from the circular joining member 50. The proximal ends 54 of each reinforcing spoke 40 are attached to the circular joining member 50 while the distal ends 56 of each reinforcing spoke 40 extend generally to the outer edge 48 of the sealing members 30 and 32.

Preferably, the reinforcing spokes 40 may be made of the same material as the circular joining member 50. The reinforcing spokes 40 may take the form of cylindrical rods, flat battens, or rectangular rods. Preferably, the circular joining member 50 and the reinforcing spokes 40 are one unitary structure laser cut from Nitinol. The headpiece 28 may also be cut from the same unitary Nitinol structure. The circular joining member 50 and the reinforcing spokes 40 may include radiopaque markers for use during fluoroscopic visualization.

Figure 3B:
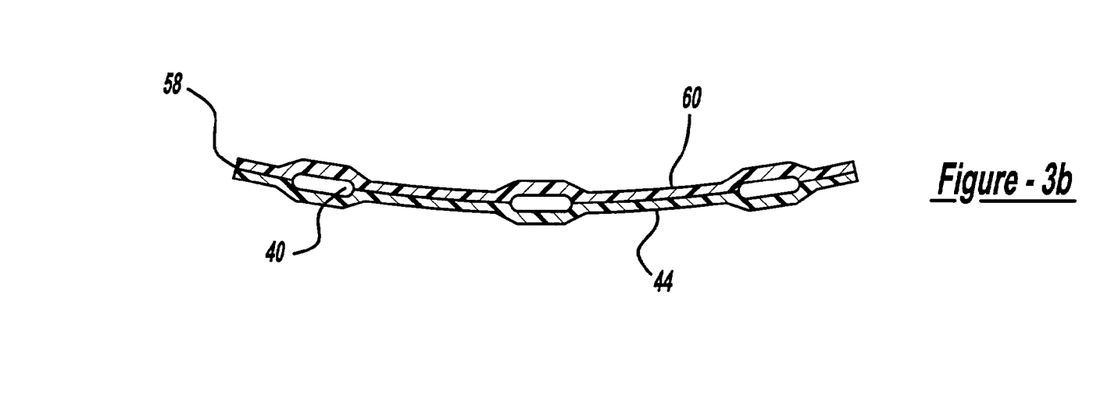
FIG. 3b is an enlarged, cross sectional view of the aneurysm neck cover showing reinforcing spokes encapsulated between two thin circular membranes.

FIG. 3b illustrates the slightly cupped configuration of a sealing member 30 and 32. The curvature may be created by a normally curved sealing member 30 and 32, but preferably, the curvature is formed by normally curved reinforcing spokes 40. Two thin circular membranes 58 are bonded to the reinforcing spokes 40 and the circular joining member 50 (not shown). Preferably, one circular membrane 58 may be attached to the reinforcing spokes 40 on the concave side 60 of the sealing members 30 and 32 while the other circular membrane 58 may be attached to the reinforcing spokes 40 on the convex side 44 of the sealing members 30 and 32, such that the circular membranes 58 encapsulate the reinforcing spokes 40 and the circular joining member 50.

Figure 4:
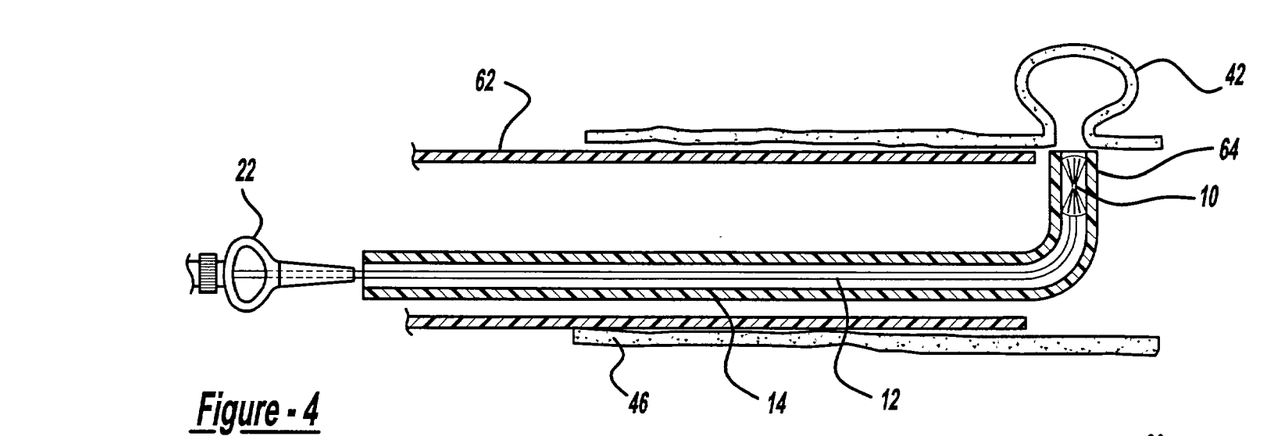
FIG. 4 is an enlarged, sectional view of the aneurysm neck cover in its collapsed configuration being positioned over an aneurysm.
Figure 5:
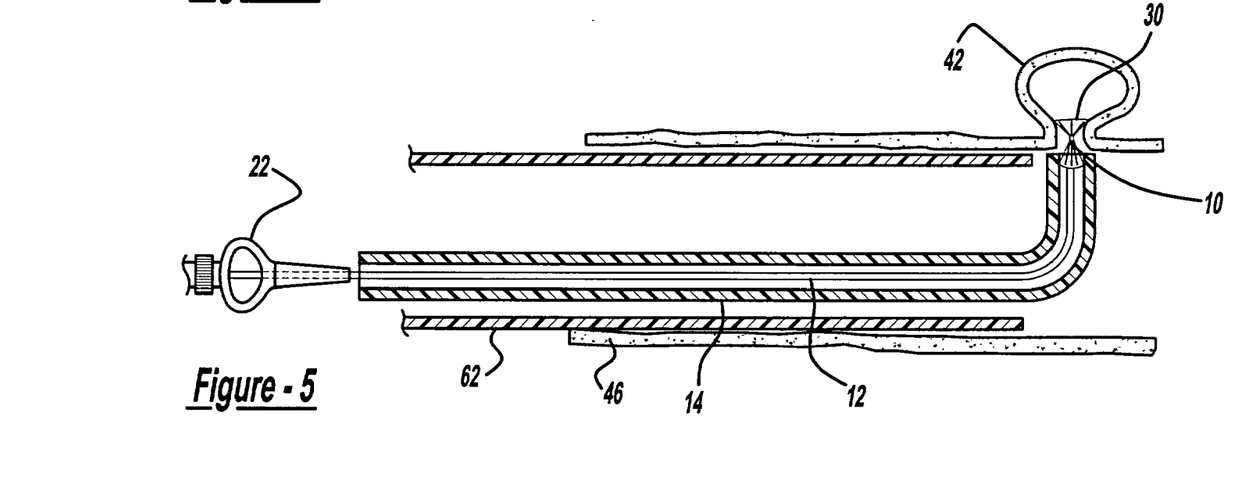
FIG. 5 is an enlarged, sectional view of the aneurysm neck cover being deployed within the aneurysm; and, FIG. 6 is an enlarged, sectional view of the aneurysm neck cover in its expanded configuration and covering the opening of the aneurysm.

FIGS. 4 through 6 illustrate the deployment of the aneurysm neck cover 10 within the aneurysm 42. FIG. 4 illustrates the aneurysm neck cover 10, the deployment catheter 12, and sheath 14 being positioned within the blood vessel 46 adjacent to the aneurysm 42 to be treated. The headpiece 28 of the aneurysm neck cover 10 is disposed within the deployment catheter 12, and the aneurysm neck cover 10 is disposed within the sheath 14 so that the sealing members 30 and 32 are in a collapsed configuration. This allows the aneurysm neck cover 10 to be inserted and transported through narrow vasculature of the human body. A delivery catheter 62 is positioned within the blood vessel 46 to guide the deployment catheter 12 to the aneurysm 42 and to protect the wall of the blood vessel 46 from damage or puncture.

FIG. 5 illustrates the distal end 64 of the sheath 14 being positioned at the mouth of the aneurysm 2. The deployment catheter 12 is then moved distally causing the first sealing member 30 to exit the distal end 64 of the sheath 14. Without the sheath 14 maintaining the aneurysm neck cover 10 in a collapsed configuration, the first sealing member 30 expands within the aneurysm 42. The thin circular membranes 58 of the first sealing member 30 contact the wall of the aneurysm 42 and form a generally fluid tight seal.

FIG. 6 illustrates fluid pressure being applied to the lumen 16 of the deployment catheter 12 thereby causing the headpiece 28 of the aneurysm neck cover 10 to exit the distal end 26 of the deployment catheter 12. The second expandable member 32 of the aneurysm neck cover 10 exits the sheath 14 and assumes its normally expanded configuration. The circular membranes 58 of the second expandable member 32 contact the wall of the adjacent blood vessel 46 and form a generally fluid tight seal. With both sealing members 30 and 32 expanded and positioned, blood is generally prevented from flowing into the aneurysm 42.

A novel system has been disclosed in which an aneurysm embolic device is used to occlude the flow of blood within an aneurysm. Although a preferred embodiment of the invention has been described, it is to be understood that various modifications may be made by those skilled in the art without departing from the scope of the present invention. These and other modifications would be apparent to those having ordinary skill in the art to which this invention relates and are intended to be within the scope of the claims which follow.

That which is claimed is:

1. A catheter-based aneurysm neck cover system for occluding the flow of blood in an aneurysm having an open mouth with an axis extending transversely through the open mouth, said aneurysm neck cover system comprising:
   a deployment catheter having a lumen extending therethrough and having proximal and distal ends; and,
   an aneurysm neck cover comprising first and second expandable sealing members, each of said expandable sealing members being formed of a membrane and is cupped shaped to form convex and concave sides with the convex side of said first expandable sealing member facing the convex side of said second expandable sealing member in the axial direction through the open mouth when the neck cover is in place at the aneurysm, said first and second sealing members each include a circular joining member and an outer edge, the diameter of said sealing members being greater than the diameter of the open mouth of the aneurysm so that each of said sealing members will overlie opposite sides of the mouth of the aneurysm when the neck cover is in place at the aneurysm, a plurality of reinforcing spokes each having a proximal end and a distal end, said reinforcing spokes being attached to said circular joining member at said proximal end and extending radially outward from said circular joining member, each said reinforcing spoke distal end extending generally to said outer edge of the first and second sealing members to form a generally umbrella-like structure, a support element extending between the first sealing member end the center of said second sealing member, and a headpiece attached to the second sealing member and retained within the distal end of said deployment catheter so that when said aneurysm neck cover is placed at a mouth of an aneurysm said umbrella-like expandable sealing members may be expanded to seal the neck of the aneurysm to prevent the flow of blood into the aneurysm.

2. A catheter-based aneurysm neck cover system as defined in claim 1, wherein each of said expandable sealing members comprises first and second circular membranes having surfaces which are bonded together and which encapsulate said circular joining member and said reinforcing spokes.

3. A catheter-based aneurysm neck cover system as defined in claim 1, wherein the support element extends between the convex side of said first expandable sealing member and the convex side of said second expandable sealing member.

4. A catheter-based aneurysm neck cover system as defined in claim 1, wherein said circular joining member and said reinforcing spokes are made from a metallic material.

5. A catheter based aneurysm neck cover system as defined in claim 1, wherein said circular membrane is made from a blood-impermeable polymer material.

6. An umbrella-like aneurysm neck cover for occluding the flow of blood in an aneurysm having an open mouth with an axis extending transversely through the open mouth, said aneurysm neck cover comprising:
    first and second expandable sealing members, said sealing members generally take the form of expandable flexible disks having a center and an outer edge, each of said expandable sealing members being formed of a membrane and is cupped shaped to form convex and concave sides with the convex side of said first expandable sealing member facing the convex side of said second expandable sealing member in the axial direction through the open mouth when the neck cover is in place at the aneurysm, each expandable sealing member including a circular joining member, the diameter of said sealing members being greater than the diameter of the open mouth of the aneurysm so that each of said sealing members will overlie opposite sides of the mouth of the aneurysm when the neck cover is in place at the aneurysm, a plurality of reinforcing spokes each having a proximal end and a distal end, said reinforcing spokes being attached to said circular joining member at said proximal end and extending radially outward from said circular joining member, each said reinforcing spoke distal end extending generally to said outer edge of the first and second expandable sealing members to form a generally umbrella-like structure, a support element having proximal and distal ends, the distal end of said support element attached to the center of said first sealing member and the proximal end of said support element attached to the center of said second sealing member so that when said aneurysm neck cover is placed at a mouth of an aneurysm said umbrella-like sealing members may be expanded to seal the neck of the aneurysm to prevent the flow of blood into the aneurysm.

7. An aneurysm neck cover as defined in claim 6, wherein each of said expandable sealing member comprises said first and second circular membranes having surfaces which are bonded together and which encapsulate said circular joining member and said reinforcing spokes.

8. An aneurysm neck cover as defined in claim 6, wherein the convex side of said first expandable sealing member is attached to the distal end of said support element and the convex side of said second expandable sealing member is attached to the proximal end of said support element.

9. An aneurysm neck cover as defined in claim 6, wherein said circular joining member and said reinforcing spokes are made from a metallic material.

10. An aneurysm neck cover as defined in claim 6, wherein said circular membrane is made from a blood-impermeable polymer material.

11. A catheter-based aneurysm neck cover system for occluding the flow of blood in an aneurysm having an open mouth with an axis extending transversely through the open mouth, said aneurysm neck cover system comprising:
    a deployment catheter having a lumen extending therethrough and having proximal and distal ends; and,
    an aneurysm neck cover comprising first and second expandable sealing members, said sealing members generally take the form of umbrella-like expandable flexible disks having a center and an outer edge and a plurality of reinforcing spokes extending between said center and said outer edge, each of said expandable sealing members being formed of a membrane and is cupped shaped to form convex and concave sides with the convex side of said first expandable sealing member facing the convex side of said second expandable sealing member in the axial direction through the open mouth when the neck cover is in place at the aneurysm, said sealing members are attached to each other at the centers of said sealing members, and a headpiece is attached to the center of said second sealing member and is retained within the distal end of said deployment catheter so that when said aneurysm neck cover is placed at a mouth of an aneurysm said sealing members may be expanded to seal the neck of the aneurysm to prevent the flow of blood within the aneurysm, the diameter of said sealing members being greater than the diameter of the open mouth of the aneurysm so that each of said sealing members will overlie opposite sides of the mouth of the aneurysm when the neck cover is in place at the aneurysm.

12. A catheter-based aneurysm neck cover system as defined in claim 11, wherein the convex side of said first expandable sealing member is attached to the convex side of said second expandable sealing member at the centers of said sealing members.

13. A catheter-based aneurysm neck cover system as defined in claim 11, wherein said expandable sealing members are generally tubular shaped prior to expansion.

14. A catheter-based aneurysm neck cover system as defined in claim 11, wherein said aneurysm neck cover includes a support element, said support element has proximal and distal ends, the center of said first expandable sealing member is attached to the distal end of said support element, the center of said second expandable sealing member is attached to the proximal end of said support element.

15. A catheter-based aneurysm neck cover system as defined in claim 14, wherein the convex side of said first expandable sealing member is attached to the distal end of said support element and the convex side of said second expandable sealing member is attached to the proximal end of said support element.

16. A catheter-based aneurysm neck cover system as defined in claim 14, wherein the concave side of said first expandable sealing member is attached to the distal end of said support element and the concave side of said second expandable sealing member is attached to the proximal end of said support element.

17. An umbrella-like aneurysm neck cover for occluding the flow of blood in an aneurysm having an open mouth with an axis extending transversely through the open mouth, said aneurysm neck cover comprising a first and a second expandable sealing member, said expandable sealing members generally take the form of umbrella-like expandable flexible disks having a center and an outer edge and a plurality of reinforcing spokes extending between said center and said outer edge, each of said expandable sealing members being formed of a membrane and is cupped shaped to form convex and concave sides with the convex side of said first expandable sealing member facing the convex side of said second expandable sealing member in the axial direction through the open mouth when the neck cover is in place at the aneurysm, said expandable sealing members are attached to each other at the centers of said sealing members so that when said aneurysm neck cover is placed at a mouth of the aneurysm said sealing members may be expanded to seal the mouth of the aneurysm to prevent the flow of blood into the aneurysm, the diameter of said sealing members being greater than the diameter of the open mouth of the aneurysm so that each of said sealing members will overlie opposite sides of the mouth of the aneurysm when the neck cover is in place at the aneurysm.

18. An aneurysm neck cover as defined in claim 17, wherein the convex side of said first expandable sealing member is attached to the oonvex side of said second expandable sealing member at the centers of said sealing members.

19. An aneurysm neck cover as defined in claim 17, wherein said expandable sealing members are generally tubular shaped prior to expansion.

20. An aneurysm neck cover as defined in claim 17, wherein said aneurysm neck cover includes a support element, said support element has proximal and distal ends, the center of said first expandable sealing member is attached to the distal end of said support element, the center of said second expandable sealing member is attached to the proximal end of said support element.

21. An aneurysm neck cover as defined in claim 20, wherein the convex side of said first expandable sealing member is attached to the distal end of said support element and the convex side of said second expandable sealing member is attached to the proximal end of said support element.

22. An aneurysm neck cover as defined in claim 20, wherein the concave side of said first expandable sealing element is attached to the distal end of said support element and the concave side of said second expandable sealing element is attached to the proximal end of said support element.

* * * * *